United States Patent
Onishi et al.

(10) Patent No.: US 6,946,557 B2
(45) Date of Patent: Sep. 20, 2005

(54) PROCESS FOR PRODUCING OPTICALLY ACTIVE ETHYL (3R, 5S, 6E)-7-[2-CYCLOPROPLY-4-(4-FLUOROPHENYL)QUINOLIN-3-YL]-3,5-DIHYDROXY-6-HEPTENOATE

(75) Inventors: Atsushi Onishi, Inaraki (JP); Koichi Murazumi, Hyogo (JP); Kozo Tachibana, Inaraki (JP)

(73) Assignees: Daicel Chemical Industries, Ltd., Osaka (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/398,915

(22) PCT Filed: Oct. 12, 2001

(86) PCT No.: PCT/JP01/09000
§ 371 (c)(1),
(2), (4) Date: Jul. 9, 2003

(87) PCT Pub. No.: WO02/30903
PCT Pub. Date: Apr. 18, 2002

(65) Prior Publication Data
US 2005/0075502 A1 Apr. 7, 2005

(30) Foreign Application Priority Data
Oct. 13, 2000 (JP) ........................................ 2000-314245

(51) Int. Cl.$^7$ ............................................. C07D 215/04
(52) U.S. Cl. ....................................... 546/173; 546/174
(58) Field of Search ................................... 546/173, 174

(56) References Cited

U.S. PATENT DOCUMENTS 5,939,552 A    8/1999    Ikeda et al.

FOREIGN PATENT DOCUMENTS

EP    747341 A1    12/1996

OTHER PUBLICATIONS

Nagamatsu, J of Chromatography A, 832, pp55–65, 1999.*
Kojima, CA 130:332232, abstract of Biological & Pharmaceutical Bulletin, 22(2), pp 142–150, 1999.*
Nagamatsu et al., Chiral Separation of a Pharmaceutical Intermediate by a Simulted Moving Bed Process, J. Chromatogr., A, (1999), vol. 832, pp. 55–65.
Chiral separation of a pharmaceutical intermediate by a simulated moving bed process, Journal of Chromatography A, 832 (1999) 55–65.

* cited by examiner

*Primary Examiner*—D. Margaret Seaman
(74) *Attorney, Agent, or Firm*—Birch, Stewart, Kolasch & Birch, LLP (57) ABSTRACT

The objective of this invention is to provide a process for producing an optically active isomer of ethyl 7-[2-cyclopropyl-4-(4-fluorophenyl)quinolin-3-yl]-3,5-dihydroxy-6-heptenoate by optically resolving an optical isomer mixture of the compound at a high productivity. The process is characterized by employing a filler comprising a carrier and a specific amount of cellulose tris (4-chlorophenyl carbamate) supported the carrier and carrying out chromatographic separation under the condition that the capacity factors have specific values.

5 Claims, 7 Drawing Sheets

PROCESS FOR PRODUCING OPTICALLY ACTIVE ETHYL (3R, 5S, 6E)-7-[2-CYCLOPROPLY-4-(4-FLUOROPHENYL) QUINOLIN-3-YL]-3,5-DIHYDROXY-6-HEPTENOATE

This application is the national phase under 35 U.S.C. §371 of PCT International Application No. PCT/JP01/09000 which has an International filing date of Oct. 12, 2001, which designated the United States of America.

TECHNICAL FIELD

The present invention relates to a process for producing optically active ethyl (3R, 5S, 6E)-7-[2-cyclopropyl-4-(4-fluorophenyl)quinolin-3-yl]-3,5-dihydroxy-6-heptenoate. More particularly, the present invention relates to a process that can produce with high productivity optically active ethyl (3R, 5S, 6E)-7-[2-cyclopropyl-4-(4-fluorophenyl) quinolin-3-yl]-3,5-dihydroxy-6-heptenoate, an intermediate product for calcium$^f$ bis {(3R, 5S, 6E)-7-[2-cyclopropyl-4-(4-fluoro-phenyl)quinolin-3-yl]-3,5-dihydroxy-6-heptenoate, which is effective in the prevention and treatment of hyperlipemia, arterial sclerosis, etc.

BACKGROUND ART

As commonly known, optically isomers usually have different actions on living bodies, in spite of the fact that they are chemically the same compound. Therefore in the fields of medicine, pharmacy and industries relating to biochemistry, to prepare optically pure compounds has become a very important subject to improve the efficacy of a medicine for a unit dosage and to prevent damage by side effects of the medicine.

Optically active statins are very effective in the prevention and treatment of hyperlipemia, arterial sclerosis, etc. For example, WO95/23125 publication discloses an industrial process for producing optically active statins.

However, with a conventional optical resolution filler that included 10–20 wt % of an active compound, the productivity was low. Consequently has been strongly desired a process for producing optically active statins, which process is more excellent in the separation productivity.

The present invention was made in the aforementioned circumstances. The objective of this invention is to provide a process for producing optically active statins, especially optically active ethyl (3R, 5S, 6E)-7-[2-cyclopropyl-4-(4-fluorophenyl)quinolin-3-yl]-3,5-dihydroxy-6-heptenoate with higher separation productivity.

DISCLOSURE OF THE INVENTION

In order to solve the aforementioned problem, the present invention provides a process for producing optically active ethyl (3R, 5S, 6E)-7-[2-cyclopropyl-4-(4-fluorophenyl) quinolin-3-yl]-3,5-dihydroxy-6-heptenoate which comprises separating an optical isomer mixture of ethyl 7-[2-cyclopropyl-4-(4-fluorophenyl)quinolin-3-yl]-3,5-dihydroxy-6-hepteno-a te by a simulated moving bed chromatography employing a filler for liquid chromatography comprising a carrier and a cellulose tris(4-chlorophenyl carbamate) supported on the carrier wherein the amount of the cellulose tris(4-chlorophenyl carbamate) is at least 23 weight % based on the total weight of the carrier and the cellulose tris (4-chlorophenyl carbamate) under the condition that capacity factors k1' and/or k2' is at least 1, the capacity factors being calculated by the following formulae:

$$k1'=(v1-v0)/v0, \text{ and}$$

$$k2'=(v2-v0)/v0$$

wherein v1 and v2 each are the respective retention volumes of the optical isomers, which are the solutes, and v0 is the dead volume.

DETAILED DESCRIPTION OF THE INVENTION

Preferred Embodiments of the invention will be explained in detail in the followings.

The present invention employs a special filler comprising a carrier and a specific amount of a cellulose tris(4-chlorophenyl carbamate) supported on the carrier, as filler for liquid chromatography.

The number average polymerization degree, which is indicated by an average number of pyranose or furanose rings per molecule, of this cellulose tris (4-chlorophenyl carbamate) is typically at least 5, preferably not less than 10. This degree does not have specific upper limits. In view of ease in handling, however, it should be not more than 1000, preferably not more than 500. If we dare mention a preferable range of the number average polymerization degree ranges, it may be between 5 and 1000, more preferably between 10 and 500.

The degree of substitution with 4-chlorophenyl carbamate groups in the cellulose tris(4-chlorophenyl carbamate) is usually 10%–100%, preferably 30%–100% and more preferably 80%–100%. A degree of less than 10% is not preferable because the resulting polymer has little ability of optical resolution. Also, a degree of less than 30% is not very preferable because optical resolution is sometimes insufficient depending upon the species and concentration of the optical isomer mixture to be separated. On the other hand, a degree in excess of 80% is preferable because particles for the filler having excellent optical resolution ability can be obtained. The degree can be determined by elemental analysis of carbon, hydrogen and nitrogen before and after the substitution.

For the carrier can be used organic and inorganic porous substances. The inorganic porous substances are preferable. Examples of the suitable organic carriers are a high molecular weight compound selected from the group consisting of polystyrene, polyacrylamide, polyacrylate, etc. Examples of the suitable inorganic carriers are silica gel, alumina, magnesia, zirconia, glass, kaolin, titanium oxide, silicate salts, hydroxyapatite, etc. The especially preferable carrier is silica gel. The particle size of silica gel usually ranges between 0.1 μm and 10 mm, preferably between 1 μm and 300 μm. The average pore size of silica gel is 10 Å–100 μm, preferably 50 Å–50,000 Å. The surface of the carrier should be treated to remove the remaining silanol that has undesirable effects on the surface. However, if the surface is not treated at all, it will not cause problems.

The amount of the cellulose tris(4-chlorophenyl carbamate) supported on the carrier is preferably at least 23 weight % based on the total weight of the cellulose tris(4-chlorophenyl carbamate) and the carrier. From the viewpoint of productivity, the amount is preferably 27 weight %, particularly preferably 27–60 weight %. The amount has no specific upper limit. However, when the amount exceeds 60 weight %, the number of the plates is lowered, which undesirably results in low efficiency in the optical separation.

The filler for liquid chromatography may be prepared either through a direct bonding of the cellulose tris(4-chlorophenyl carbamate) with the carrier, or through coating the carrier with a solution including the cellulose tris(4-chlorophenyl carbamate) and removing the solvent by distillation. The solvent may be any organic solvent that is commonly used, as long as it can dissolve the cellulose tris(4-chlorophenyl carbamate).

Moreover, by forming further chemical bonds between the carrier and the applied cellulose tris(4-chlorophenyl carbamate), and between the molecules of the cellulose tris(4-chlorophenyl carbamate) itself on the carrier, the compound may be firmly fixed on the carrier. The further chemical bonds may be formed through reactions by utilizing another component, by irradiating the compound on the carrier with light, radiant rays such as γ ray or electromagnetic waves such as micro wave, or by forming radicals with a free-radical initiator.

The optically active compounds that can be produced by the method in accordance with this invention include ethyl (3R, 5S, 6E)-7-[2-cyclopropyl-4-(4-fluorophenyl)quinolin-3-yl]-3,5-dihydroxy-6-heptenoate represented by the following formula (I).

(I)

In the process of this invention, an optical isomer mixture of ethyl 7-[2-cyclopropyl-4-(4-fluorophenyl)quinolin-3-yl]-3,5-dihydroxy-6-heptenoate is subjected to optical resolution by a simulated moving bed chromatography employing a super critical liquid or an ordinary solvent for the mobile phase. The ordinary solvent is particularly suitable for the mobile phase of this invention. An example of the simulated moving bed chromatographic separation method will be given in the followings. It should be noted that the separation method in accordance with the invention is not limited to the example and that the conditions including the cycle time may be set at the operator's discretion for optimizing the operation, as disclosed by, e.g. WO 00/25885.

Separation through adsorption by a simulated moving bed chromatography is effected by continuously carrying out an adsorption step, a concentration step, a desorption step and an eluent recovery step in circulation.

(1) Adsorption Step

An optical isomer mixture solution is contacted with a filler, whereby an optically active isomer easily adsorbed by the filler (strongly adsorbable substance) is adsorbed by the filler while the other optical isomer not easily adsorbed by the filler (poorly adsorbable substance) goes into raffinate, which is recovered together with the eluent.

(2) Concentration Step

The filler, which has adsorbed the strongly adsorbable substance, is contacted with a portion of extract as will be described below, the poorly adsorbable substance retained on the filler is expelled, and thus the adsorbable substance is concentrated.

(3) Desorption Step

The filler, which has the concentrated strongly adsorbable substance is contacted with the eluent, and the substance is expelled from the filler and taken out of the simulated moving bed apparatus together with the eluent as extract.

(4) Eluent Recovery Step

The filler that contains substantially only the eluent is contacted with a portion of the raffinate, and a portion of the eluent contained in the filler is recovered as an eluent recovery.

Figure 1:
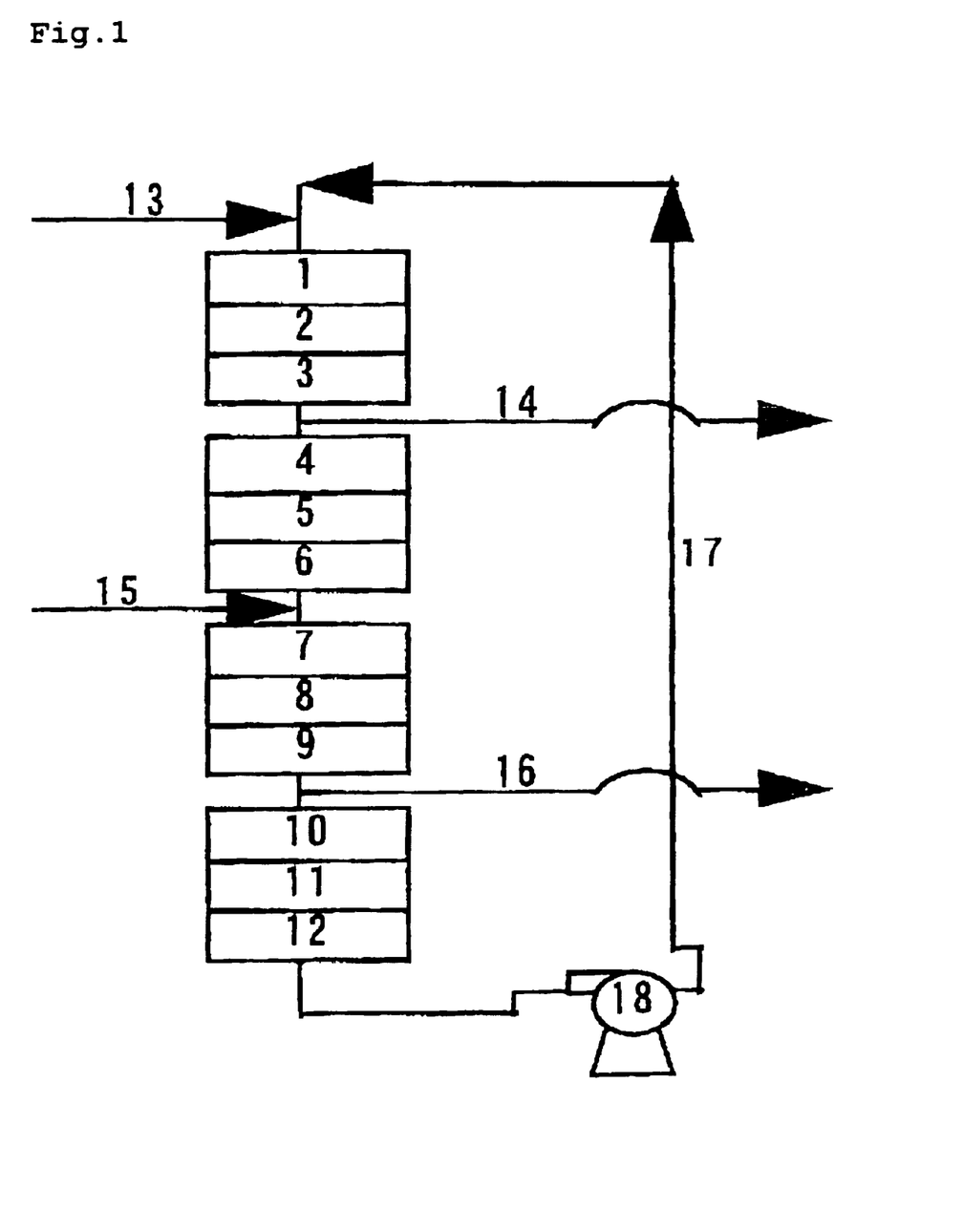
FIG. 1 is a schematic illustration that shows an example of a simulated moving bed chromatographic separation apparatus employed in this invention. In this figure, reference numerals 1–12 denote unit columns, reference numeral 13 denotes an eluent supply conduit, reference numeral 14 an extract draw-out conduit, reference numeral 15 an optical isomer-mixture supply conduit, reference numeral 16 a raffinate draw-out conduit, reference numeral 17 a circulation conduit, and reference numeral 18 a circulation pump.
Figure 2:
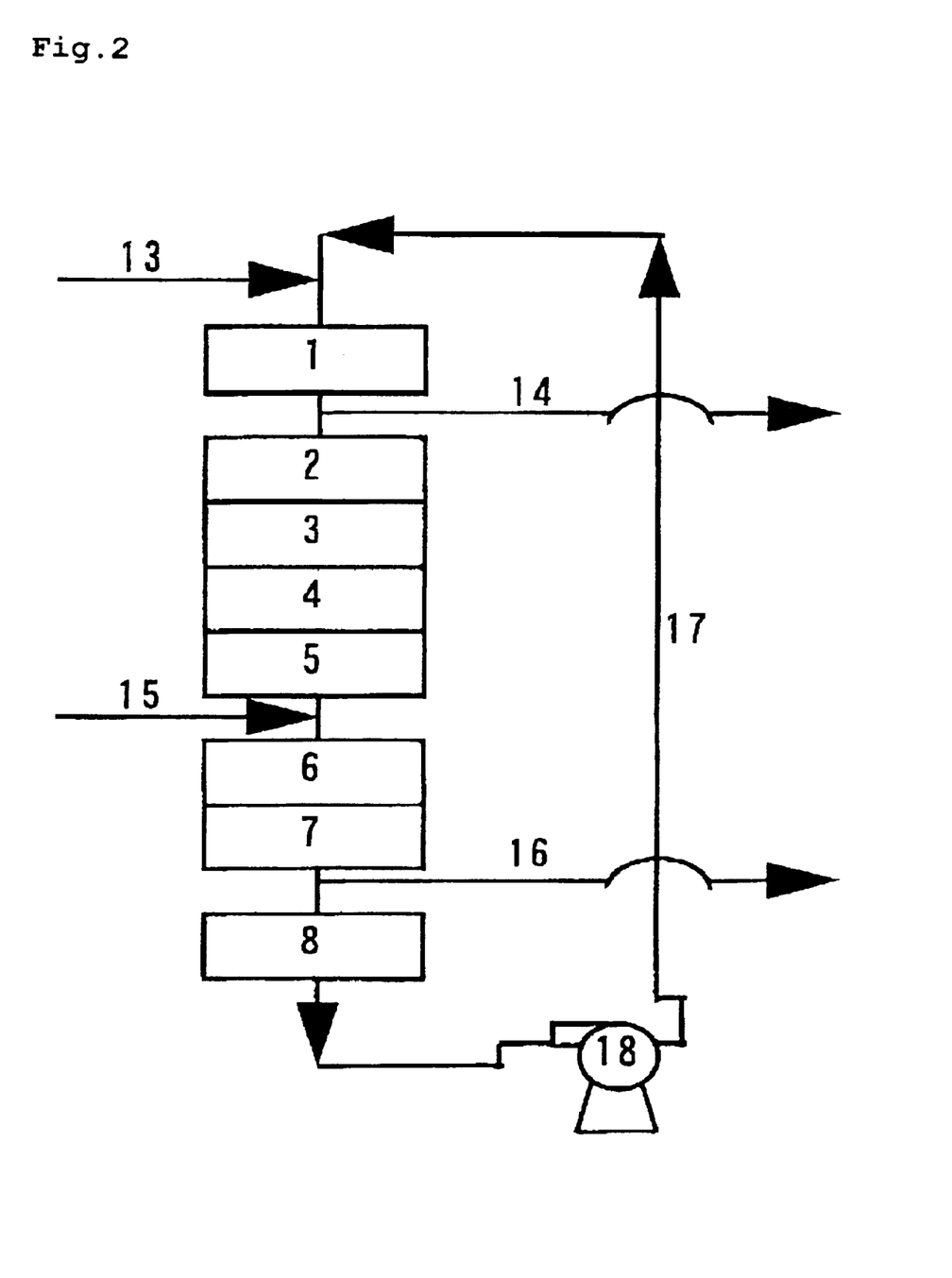
FIG. 2 is a schematic illustration that shows another example of a simulated moving bed chromatographic separation apparatus employed in this invention.

Now the procedures are explained in detail with reference to the attached drawings. FIG. 1 is a schematic illustration that shows an example of the simulated moving bed apparatus employed in this invention. FIG. 2 is a schematic illustration that shows another example of the simulated moving bed apparatus employed in this invention.

In FIG. 1, the beds, which are the main part of the simulated moving bed apparatus, are divided into 12 (twelve) unit columns. In FIG. 2, the apparatus has 8 (eight) unit columns. The number of the unit columns and the size of each unit column are not limited to the above-mentioned, but decided depending on the factors such as the composition and flow rate of the optical isomer mixture solution, and the pressure loss and the dimensions of the apparatus.

In FIG. 1, unit columns 1–12 are filled with a filler and they are mutually connected with fluid passages. The eluent is introduced through eluent supply conduit 13, the extract is taken out through extract conduit 14, the mixture solution containing optical isomers is supplied via conduit 15, the raffinate is taken out through raffinate conduit 16, and the fluid is recirculated through recirculation conduit 17 by means of pump 18.

In the state of unit columns 1–12 and conduits 13–16 as shown in FIG. 1, desorption is done in unit columns 1–3, concentration in unit columns 4–6, adsorption in unit columns 7–9, and eluent recovery in unit columns 10–12. In the simulated moving bed system like this, the working positions of the respective supply conduits and the respective taking-out conduits are shifted one unit column by one unit column in the fluid flow direction at a constant time interval by operation of valves. In the next stage, therefore, desorption is done in unit columns 2–4, concentration in unit columns 5–7, adsorption in unit columns 8–10, and eluent recovery in unit columns 11–1. By repeating this operation successively, each step is carried out in a set of unit columns that are shifted one column by one column. Thus optical resolution of an optical isomer mixture is efficiently achieved.

In the state of unit columns 1–8 and conduits 13–16 as shown in FIG. 2, eluent recovery is done in unit column 1, adsorption in unit columns 2–5, concentration in unit columns 6–7, and desorption in unit column 8. In the simulated moving bed system like this, the working positions of the respective supply conduits and the respective taking-out conduits are shifted one unit column by one unit column in the fluid flow direction at a constant time interval by operation of valves. In the next stage, therefore, desorption is done in unit column 2, concentration in unit columns 3–6, adsorption in unit columns 7–8, and eluent recovery in unit column 1. By repeating this operation successively, each step is carried out in a set of unit columns that are shifted one column by one column. Thus optical resolution of an optical isomer mixture is efficiently achieved.

In the simulated moving bed chromatography in accordance with this invention, the chromatographic separation should be carried out under the condition that capacity factors k1' and/or k2' is at least 1. In this specification "k1'" and "k2'" mean the capacity factors calculated by the following formulae:

$$k1'=(v1-v0)/v0 \quad (1)$$

$$k2'=(v2-v0)/v0 \quad (2)$$

wherein each of v1 and v2 is the retention volume of each optical isomer, which is an eluted component, and v0 is a dead volume.

When both of capacity factors k1' and k2' are less than 1, the productivity is lowered, which is undesirable. Either of k1' and k2' should be at least 1. From the viewpoint of improving productivity, more preferable is that both of the factors are at least 1.

EXAMPLES

Synthesizing Example 1

Preparation of an HPLC Column Containing a Filler that Includes 24 Weight % of Cellulose tris (4-chlorophenyl-carbamate)

(1) Surface Treatment of Silica Gel

A porous silica gel (the average particle size: 20 μm) was subjected to an aminopropyl silane treatment (APS treatment) through a reaction of the silica gel with 3-aminopropyl triethoxy silane by a known method. Reaction of the obtained APS-treated silica gel with 3,5-dimethyl phenyl isocyanate produced a carbamoyl-surface-treated silica gel.

(2) Synthesis of Cellulose tris(4-chlorophenyl carbamate)

Under nitrogen atmosphere, 100 g of cellulose and 714.1 g (2.5 equivalent weight) of 4-chlorophenyl carbamate in 3.8 liters of dried pyridine were heated and stirred for 60 hours at the reflux temperature of pyridine. The solution was poured into 40 liters of 2-propanol. The formed precipitate was isolated by filtration with a glass filter, washed several times with 2-propanl, and then vacuum-dried at 80° C. for 15 hours. The collected was a yellowish white solid product, which weighed 287 g. The yield was 75%.

(3) Preparation of a Filler Made of Silica Gel Supporting 24 Weight % of Cellulose tris(4-chlorophenyl carbamate)

120 g of cellulose tris(4-chlorophenyl carbamate) obtained in step (2) above was dissolved in 600 ml of acetone. 380 g of the treated silica gel prepared in step (1) above was uniformly coated with the half amount of this polymer solution. The acetone was vacuum-distilled off from the coated silica gel at 40° C. for 45 minutes under 40 kPa. The silica gel was again coated with the remaining half of the polymer solution, and acetone was vacuum-distilled off in the same way. Then, the aimed filler made of silica gel supporting 24 weight % of cellulose tris(4-chlorophenyl carbamate) was obtained.

(4) Preparation of a Filled HPLC Column from the Prepared Filler

A stainless steel column of 25 cm in length and 0.46 cm in inner diameter was filled with the filler made of silica gel supporting cellulose tris(4-chlorophenylcarbamate), which was prepared in step (3) above, by the slurry method. Then a separation column for optical isomers was obtained.

Synthesizing Example 2

Preparation of an HPLC Column Containing a Filler that Includes 30 Weight % of Cellulose tris (4-chlorophenyl-carbamate)

(1) Surface Treatment of Silica Gel

The surface treatment was carried out in the same way as explained in Synthesizing Example 1 (1).

(2) Synthesis of Cellulose tris(4-chlorophenyl carbamate)

Cellulose tris(4-chlorophenyl carbamate) was synthesized in the same way as explained in Synthesizing Example 1 (2).

(3) Preparation of a Filler Made of Silica Gel Supporting 30 Weight % of Cellulose tris(4-chlorophenyl carbamate)

150 g of cellulose tris(4-chlorophenyl carbamate) obtained in step (2) above was dissolved in 800 ml of acetone. 350 g of the treated silica gel prepared in step (1) above was uniformly coated with this polymer solution. The acetone was vacuum-distilled off from the coated silica gel at 40° C. for 30 minutes under 40 kPa. Then, the aimed filler made of silica gel supporting 30 weight % of cellulose tris(4-chlorophenyl carbamate) was obtained.

(4) Preparation of a Filled HPLC Column from the Prepared Filler

A stainless steel column of 25 cm in length and 0.46 cm in inner diameter was filled with the filler made of silica gel supporting cellulose tris(4-chlorophenylcarbamate), which was prepared in step (3) above, by the slurry method. Then a separation column for optical isomers was obtained.

Synthesizing Example 3

Preparation of an HPLC Column Containing a Filler that Includes 20 Weight % of Cellulose tris (4-chlorophenyl carbamate)

(1) Surface Treatment of Silica Gel

The surface treatment was carried out in the same way as explained in Synthesizing Example 1 (1).

(2) Synthesis of Cellulose tris(4-chlorophenyl carbamate)

Cellulose tris(4-chlorophenyl carbamate) was synthesized in the same way as explained in Synthesizing Example 1 (2).

(3) Preparation of a Filler Made of Silica Gel Supporting 20 Weight % of Cellulose tris(4-chlorophenyl carbamate)

100 g of cellulose tris(4-chlorophenyl carbamate) obtained in step (2) above was dissolved in 600 ml of acetone. 400 g of the treated silica gel prepared in step (1) above was uniformly coated with this polymer solution. The acetone was vacuum-distilled off from the coated silica gel at 40° C. for 30 minutes under 40 kPa. Then, the aimed filler made of silica gel supporting 20 weight % of cellulose tris(4-chlorophenyl carbamate) was obtained.

(4) Preparation of a Filled HPLC Column from the Prepared Filler

A stainless steel column of 25 cm in length and 0.46 cm in inner diameter was filled with the filler made of silica gel supporting cellulose tris (4-chlorophenylcarbamate), which was prepared in step (3) above, by the slurry method. Then a separation column for optical isomers was obtained.

Working Example 1

Measurement of the Capacity Factors and Simulated Moving Bed Chromatographic Separation Using the Column and the Filler Made in Synthesizing Example 1

Figure 3:
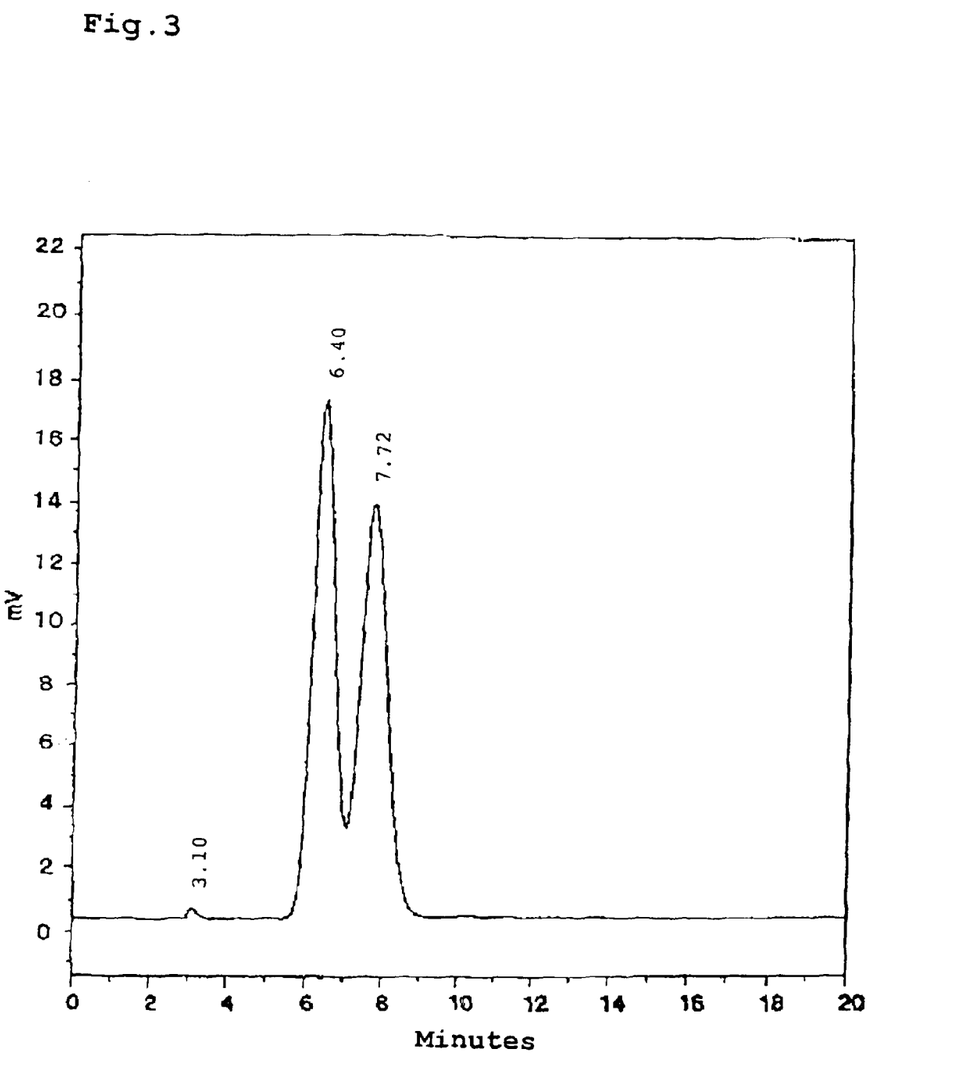
FIG. 3 is a chromatogram obtained in Working Example 1.

Ethyl (3R, 5S, 6E)-7-[2-cyclopropyl-4-(4-fluorophenyl) quinolin-3-yl]-3,5-dihydroxy-6-heptenoate represented by formula (I) was analyzed with the HPLC column made in Synthesizing Example 1, which HPLC column was fixed in a liquid chromatographic apparatus. The conditions of the analysis and the capacity factors obtained are shown in Table 1. The chromatogram is shown in FIG. 3.

Eight (8) stainless steel columns, each being 1.0 cm in inner diameter and 10 cm in length, were filled by the slurry method with the filler prepared in Synthesizing Example 1. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 2.

Mobile phase: n-hexane/2-propanol 68/32 (vol.) mixture
Column temperature: 40° C.
Supply rate of feedstock: 1.15 ml/min.
Flow rate of raffinate: 2.97 ml/min.
Flow rate of extract: 10.43 ml/min.
Flow rate of eluent: 12.24 ml/min.
Step time: 1.5 min.
Concentration of feedstock: 20 mg/ml-mobile phase
Flow rate in zone I: 14.40 ml/min.
Flow rate in zone II: 3.97 ml/min.
Flow rate in zone III: 5.13 ml/min.
Flow rate in zone IV: 2.16 ml/min.

Working Example 2

Measurement of the Capacity Factors and Simulated Moving Bed Chromatographic Separation Using the Column and the Filler Made in Synthesizing Example 2

Figure 4:
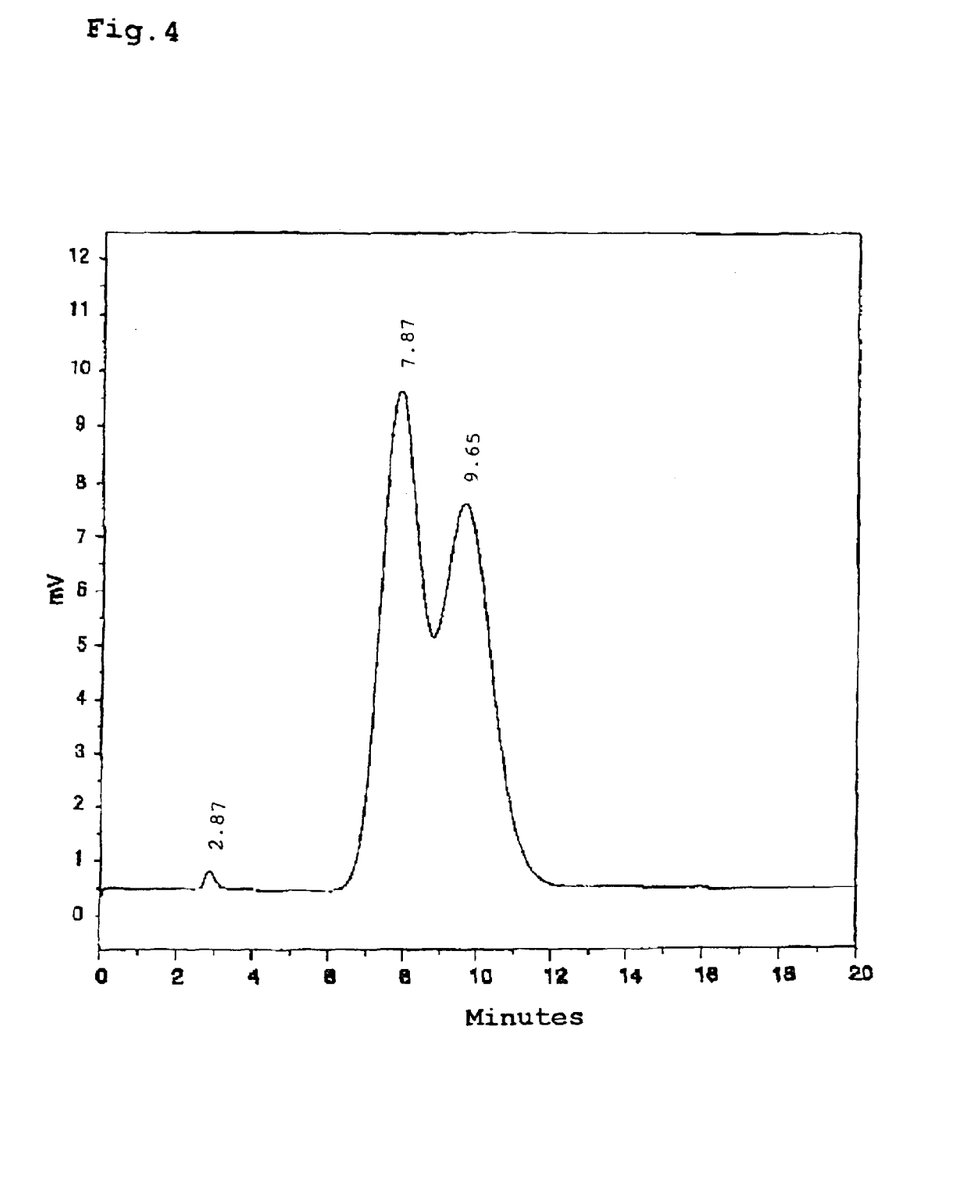
FIG. 4 is a chromatogram obtained in Working Example 2.

Ethyl (3R, 5S, 6E)-7-[2-cyclopropyl-4-(4-fluorophenyl) quinolin-3-yl]-3,5-dihydroxy-6-heptenoate represented by formula (I) was analyzed with the HPLC column made in Synthesizing Example 2, which HPLC column was fixed in a liquid chromatographic apparatus. The conditions of the analysis and the capacity factors obtained are shown in Table 1. The chromatogram is shown in FIG. 4.

Eight (8) stainless steel columns, each being 1.0 cm in inner diameter and 10 cm in length, were filled by the slurry method with the filler prepared in Synthesizing Example 1. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 2. The chromatogram is shown in FIG. 4.

Mobile phase: n-hexane/2-propanol 68/32 (vol.) mixture
Column temperature: 40° C.
Supply rate of feedstock: 1.18 ml/min.
Flow rate of raffinate: 4.59 ml/min.
Flow rate of extract: 17.15 ml/min.
Flow rate of eluent: 20.56 ml/min.
Step time: 1.5 min.
Concentration of feedstock: 20 mg/ml-mobile phase
Flow rate in zone I: 23.58 ml/min.
Flow rate in zone II: 6.43 ml/min.
Flow rate in zone III: 7.61 ml/min.
Flow rate in zone IV: 3.02 ml/min.

Comparative Example 1

Measurement of the Capacity Factors and Simulated Moving Bed Chromatographic separation Using the Column and the Filler Made in Synthesizing Example 1

Figure 5:
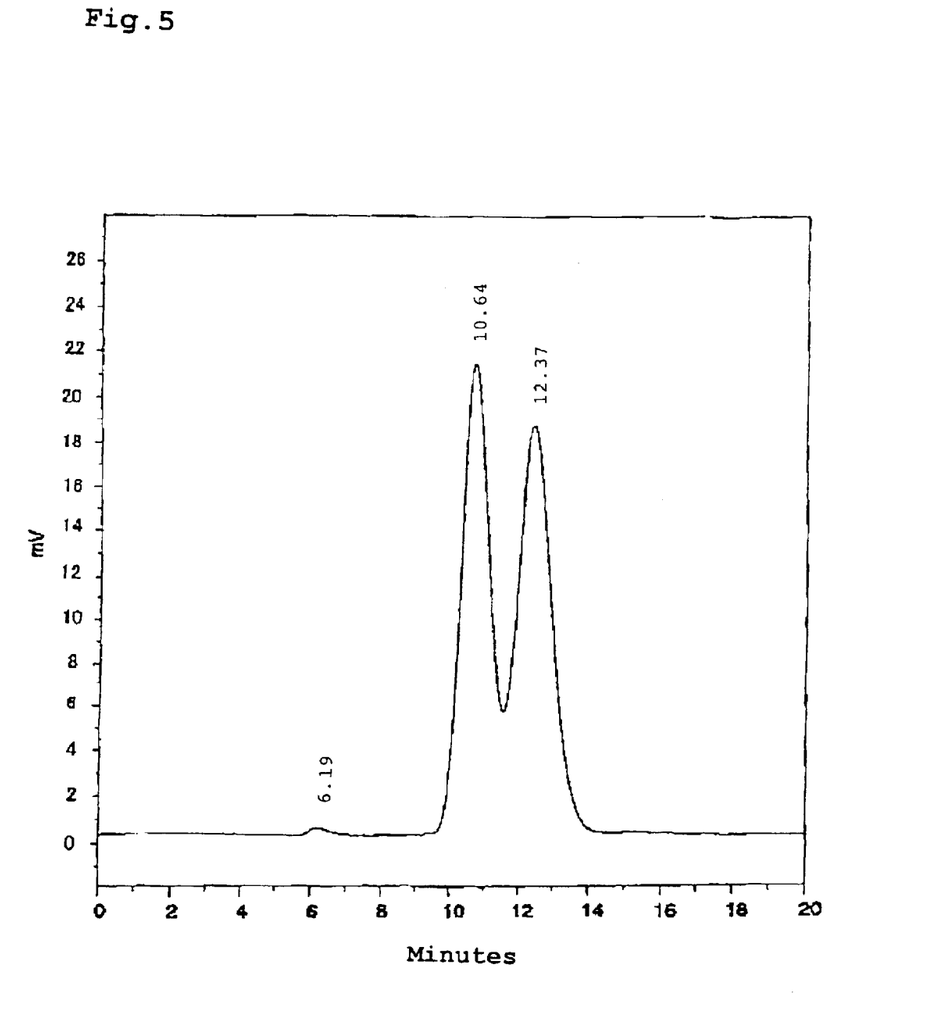
FIG. 5 is a chromatogram obtained in Comparative Example 1.

Ethyl (3R, 5S, 6E)-7-[2-cyclopropyl-4-(4-fluorophenyl) quinolin-3-yl]-3,5-dihydroxy-6-heptenoate represented by formula (I) was analyzed with the HPLC column made in Synthesizing Example 1, which HPLC column was fixed in a liquid chromatographic apparatus. The conditions of the analysis and the capacity factors obtained are shown in Table 1. The chromatogram is shown in FIG. 5.

Eight (8) stainless steel columns, each being 1.0 cm in inner diameter and 10 cm in length, were filled by the slurry method with the filler prepared in Synthesizing Example 1. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 2.

Mobile phase: n-hexane/2-propanol 55/45 (vol.) mixture
Column temperature: 40° C.
Supply rate of feedstock: 0.59 ml/min.
Flow rate of raffinate: 1.90 ml/min.
Flow rate of extract: 6.55 ml/min.
Flow rate of eluent: 7.87 ml/min.
Step time: 1.5 min.
Concentration of feedstock: 20 mg/ml-mobile phase
Flow rate in zone I: 9.43 ml/min.
Flow rate in zone II: 2.88 ml/min.
Flow rate in zone III: 3.46 ml/min.
Flow rate in zone IV: 1.56 ml/min.

Comparative Example 2

Measurement of the Capacity Factors and Simulated Moving Bed Chromatographic Separation Using the Column and the Filler Made in Synthesizing Example 2

Ethyl (3R, 5S, 6E)-7-[2-cyclopropyl-4-(4-fluorophenyl) quinolin-3-yl]-3,5-dihydroxy-6-heptenoate represented by formula (I) was analyzed with the HPLC column made in Synthesizing Example 2, which HPLC column was fixed in a liquid chromatographic apparatus. The conditions of the analysis and the capacity factors obtained are shown in Table 1. The chromatogram is shown in FIG. 6.

Figure 6:
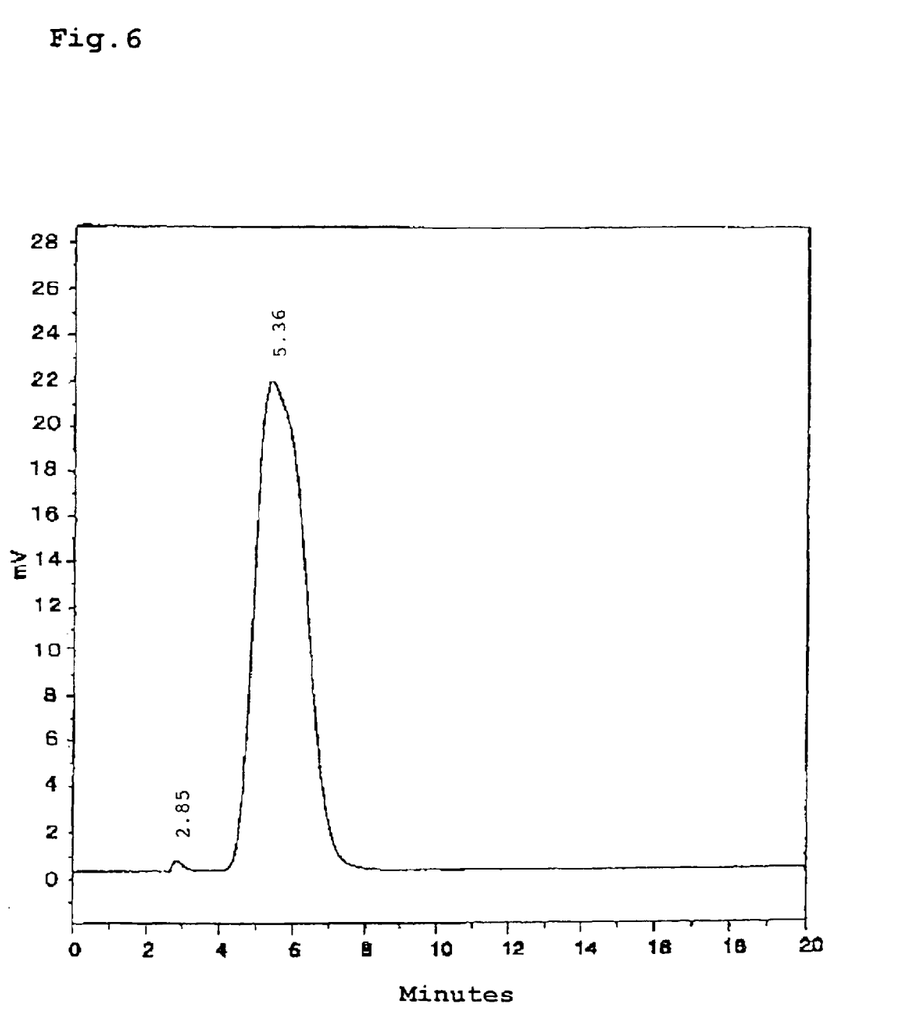
FIG. 6 is a chromatogram obtained in Comparative Example 2.

As understood from FIG. 6, the separation of the enatiomers could not be done under this condition.

Comparative Examples 3

Measurement of the Capacity Factors and Simulated Moving Bed Chromatographic Separation Using the Column and the Filler Made in Synthesizing Example 3

Figure 7:
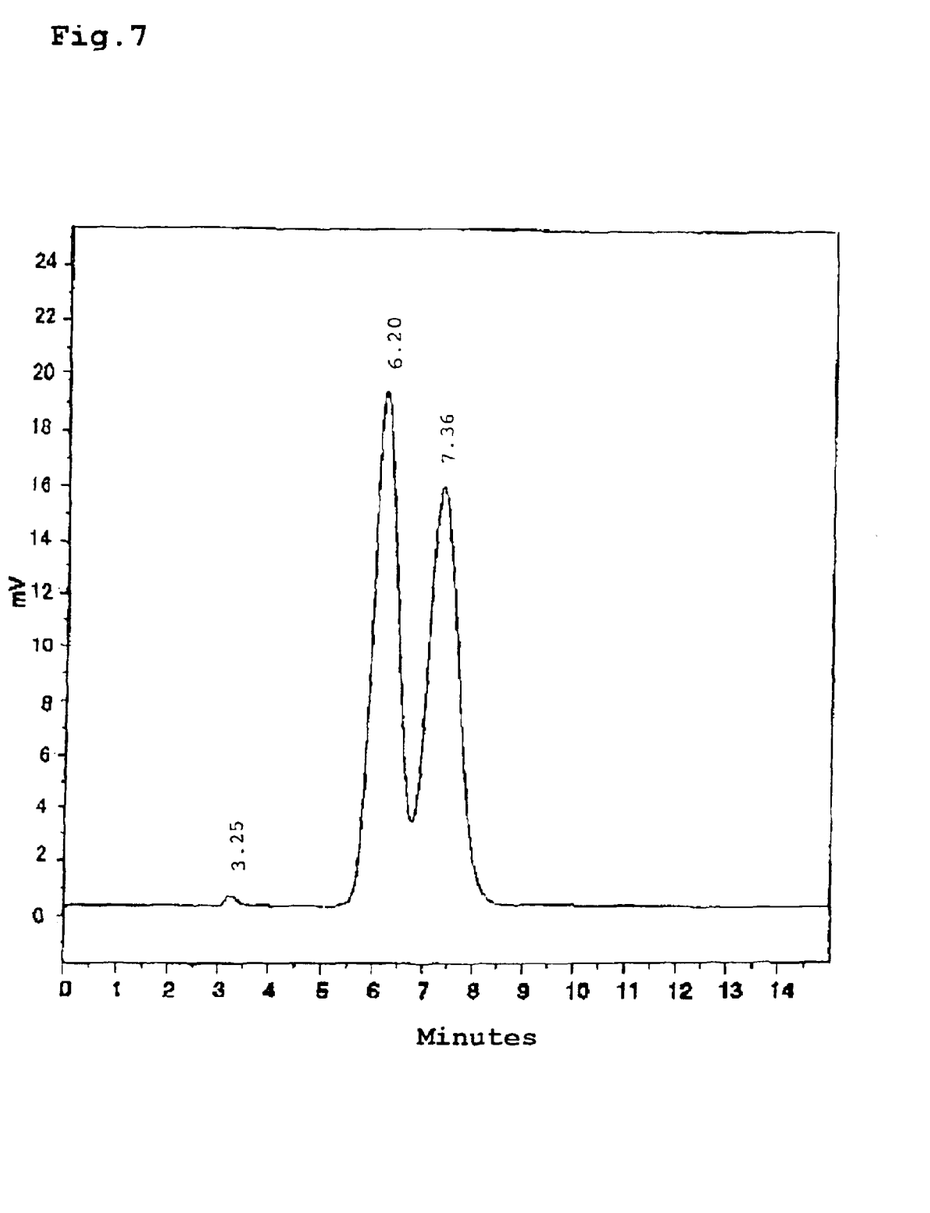
FIG. 7 is a chromatogram obtained in Comparative Example 3.

Ethyl (3R, 5S, 6E)-7-[2-cyclopropyl-4-(4-fluorophenyl)quinolin-3-yl]-3,5-dihydroxy-6-heptenoate represented by formula (I) was analyzed with the HPLC column made in Synthesizing Example 3, which HPLC column was fixed in a liquid chromatographic apparatus. The conditions of the analysis and the capacity factors obtained are shown in Table 1. The chromatogram is shown in FIG. 7.

Eight (8) stainless steel columns, each being 1.0 cm in inner diameter and 10 cm in length, were filled by the slurry method with the filler prepared in Synthesizing Example 3. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 2.

Mobile phase: n-hexane/2-propanol 68/32 (vol.) mixture
Column temperature: 40° C.
Supply rate of feedstock: 1.05 ml/min.
Flow rate of raffinate: 2.59 ml/min.
Flow rate of extract: 9.32 ml/min.
Flow rate of eluent: 10.86 ml/min.
Step time: 1.5 min.
Concentration of feedstock: 20 mg/ml-mobile phase
Flow rate in zone I: 12.80 ml/min.
Flow rate in zone II: 3.48 ml/min.
Flow rate in zone III: 4.53 ml/min.
Flow rate in zone IV: 1.94 ml/min.

TABLE 1

| Column | Amount of the supported | Conditions of analysis | k1' k2' | Chromatogram |
|---|---|---|---|---|
| W. Ex. 1 | Made in S.E. 1 | 24 wt % | (1)* | 1.06 1.49 | FIG. 3 |
| W. Ex. 2 | Made in S.E. 2 | 30 wt % | (1)* | 1.74 2.36 | FIG. 4 |
| C. Ex. 1 | Made in S.E. 1 | 24 wt % | (2)* | 0.51 0.68 | FIG. 5 |
| C. Ex. 2 | Made in S.E. 2 | 30 wt % | (3)* | 0.88 — | FIG. 6 |
| C. Ex. 3 | Made in S.E. 3 | 20 wt % | (1)* | 0.91 1.26 | FIG., 7 |

*The conditions of the analyses
(1) Mobile phase: n-hexane/2-propanol 68/32 (vol.) mixture, Flow rate: 1.0 ml/min., Temperature: 40° C., Detection: 254 nm, Injection amount: 1.5 mg/ml (mobile phase) × 2.5 μl
(2) Mobile phase: n-hexane/2-propanol 55/45 (vol.) mixture, Flow rate: 0.5 ml/min., Temperature: 40° C., Detection: 254 nm, Injection amount: 1.5 mg/ml (mobile phase) × 2.5 μl
(3) Mobile phase: n-hexane/2-propanol 55/45 (vol.) mixture, Flow rate: 1.0 ml/min., Temperature: 40° C., Detection: 254 nm, Injection amount: 1.5 mg/ml (mobile phase) × 2.5 μl The value of k' was calculated by the following formula:

$$k' = (v - v0)/v0$$

wherein v0 is the retention volume of tri-tert-benzyl benzene, v is the retention volume of the solute.

TABLE 2

| | W. Ex. 1 | W. Ex. 2 | C. Ex. 1 | C. Ex. 2 | C. Ex. 3 |
|---|---|---|---|---|---|
| | | | Mobile phase | | |
| | (1) | (1) | (2) | (2) | (1) |
| Optical purity of raffinate (% ee) | 99.5 | 99.4 | — | —*2 | 99.5 |
| Optical purity of extract (% ee) | 94.7 | 94.8 | — | —*2 | 94.6 |
| Productivity (kg-rac./kg-CSP/day)*1 | 0.88 | 0.90 | 0.45 | —*2 | 0.80 |

The mobile phases
(1) n-hexane/2-propanol 68/32 (vol.) mixture
(2) n-hexane/2-propanol 55/45 (vol.) mixture
*1The weight (kg) of a racemic compound that can be separated with 1 kg of the filler per day.
*2Because the mixture was not separated in the liquid chromatographic apparatus using the single column, the production with the small-sized simulated moving bed chromatographic apparatus was not carried out.

INDUSTRIAL APPLICABILITY

This invention provides a process for continuously and efficiently isolating ethyl (3R, 5S, 6E)-7-[2-cyclopropyl-4-(4-fluorophenyl)quinolin-3-yl]-3,5-dihydroxy-6-heptenoate by a simulated moving bed chromatographic separation utilizing a filler having an excellent optical resolution ability. This process can substantially reduce the industrial production cost.

We claim:

1. A process for producing optically active ethyl (3R, 5S, 6E)-7-[2-cyclopropyl-4-(4-fluorophenyl)quinolin-3-yl]-3,5-dihydroxy-6-heptenoate which comprises separating an optical isomer mixture of ethyl 7-[2-cyclopropyl-4-(4-fluorophenyl)quinolin-3-yl]-3,5-dihydroxy-6-heptenoate by a simulated moving bed chromatography employing a filler for liquid chromatography comprising a carrier and a cellulose tris(4-chlorophenyl carbamate) supported on the carrier wherein the amount of the cellulose tris(4-chlorophenyl carbamate) is at least 23 weight % based on the total weight of the carrier and the cellulose tris(4-chlorophenylcarbamate) under the condition that capacity factors k1' and/or k2' is at least 1, the capacity factors being calculated by the following formulae:

$$k1' = (v1 - v0)/v0, \text{ and}$$

$$k2' = (v2 - v0)/v0$$

wherein v1 and v2 each are the respective retention volumes of the optical isomers, which are the solutes, and v0 is the dead volume.

2. The process as claimed in claim 1, wherein the cellulose tris(4-chlorophenyl carbamate) has a number average polymerization degree of at least 5.

3. The process as claimed in claim 1, wherein the degree of substitution with 4-chlorophenyl carbamate groups in the cellulose tris(4-chlorophenyl carbamate) is 10%–100%.

4. The process as claimed in claim 1, wherein the carrier is a porous inorganic substance.

5. The process as claimed in claim 1, wherein the carrier is silica gel.

* * * * *